United States Patent [19]

Cattani

[11] Patent Number: 5,039,405
[45] Date of Patent: Aug. 13, 1991

[54] DISCONNECTOR FOR THE PROTECTION OF THE WATERMAIN, WITH PARTICULAR REFERENCE TO MEDICAL PLANTS

[75] Inventor: Augusto Cattani, Parma, Italy

[73] Assignee: Officine Augusto Cattini & C. S.p.A., Parma, Italy

[21] Appl. No.: 482,199

[22] Filed: Feb. 20, 1990

[30] Foreign Application Priority Data

Jun. 3, 1989 [IT] Italy ................................ 40036 A/89

[51] Int. Cl.⁵ ............................................. F16L 55/07
[52] U.S. Cl. .................................... 210/167; 137/215; 137/386; 137/583; 433/92
[58] Field of Search ............... 137/215, 216, 385, 563; 210/194, 167; 433/92, 97

[56] References Cited

U.S. PATENT DOCUMENTS

| | | | |
|---|---|---|---|
| 3,482,313 | 12/1969 | Stram | 433/92 |
| 3,754,741 | 8/1973 | Whitehurst | 137/563 |
| 4,245,989 | 1/1981 | Folkenroth et al. | 433/92 |
| 4,293,300 | 10/1981 | Cattani | 433/92 |
| 4,344,756 | 8/1982 | Folkenroth et al. | 433/92 |
| 4,386,910 | 6/1983 | Cattani | 433/92 |
| 4,414,998 | 11/1983 | Rudler et al. | 137/216 |
| 4,580,978 | 4/1986 | Motola et al. | 433/92 |
| 4,684,345 | 8/1987 | Cattani | 433/92 |

*Primary Examiner*—Robert A. Dawson
*Assistant Examiner*—Joseph Orodge
*Attorney, Agent, or Firm*—Darby & Darby

[57] ABSTRACT

The present invention relates to a back-flow prevention device for use with a water supply for supplying water to dental instruments within a dental clinic for preventing bacteria contamination of a water source feeding water supply. The device provides no mechanical connection between the water source and the water supply.

3 Claims, 1 Drawing Sheet

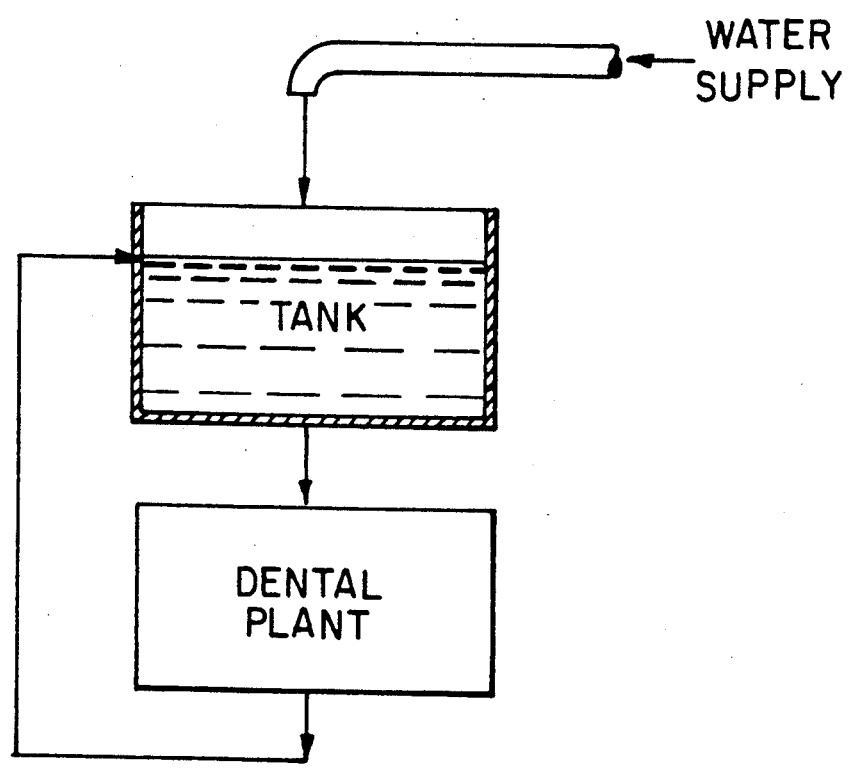

DISCONNECTOR FOR THE PROTECTION OF THE WATERMAIN, WITH PARTICULAR REFERENCE TO MEDICAL PLANTS

BACKGROUND OF THE INVENTION

The invention relates to a back flow prevention system for the protection of the watermain, with particular application in dental clinics.

In dental clinics, and in particular during dental bridgework, it is frequently necessary to use water from the watermain; a typical instance, which will be used during the following description and which is to be considered not as an indication of the limits of the back flow prevention system but purely as an apt example, is the liquid ring pump in aspirating dental instruments. These pumps are used to aspirate fluids that naturally abound in bacteria and pollutants. For this reason it is absolutely necessary, and in many cases a legal requirement, to prevent these bacteria and pollutants from getting into the watermain; this can happen both in cases of malfunction of the pump (for example, through accidental function inversion) and during times when the pump is not in use.

In order to avoid such accidents filters are sometimes used, which are quite effective as regards pollutants, but which produce unsatisfactory results as far as bacterial pollution is concerned. Also used for this purpose are complex-type valves which prevent the return of the fluid towards the watermain in the case of siphoning or flow inversion. However, these valves do not guarantee absolute security with regard to halting the bacteria which, even if only in certain circumstances, can reach the watermain.

SUMMARY OF THE INVENTION

The aim of the invention is to eliminate the above-described drawbacks by providing an instrument which absolutely prevents the introduction of bacteria and other pollutants into the watermain.

A further aim of the invention is to provide a back flow prevention system of simple and economical construction which can be installed in existing plants.

These aims and others besides are attained by the back flow prevention system in question, made according to the specifications indicated in the claims. A notable advantage of the invention is that it permits recycling of the water used by the medical plant.

Further characteristics and advantages of the invention will emerge during the detailed description that follows, whose aim is simply to provide an example of the use of the back flow prevention system in question, and not to indicate its limitations. The back flow prevention system in question envisages, in essence, the use of an air gap which is interposed between the watermain and the dental clinic which uses water from the network. In this way, either in the case of an interruption in the drawing of the water, or in the case of siphoning or flow inversion, a secure barrier exists which prevents both bacteria and any other pollutants from penetrating into the watermain. This does not occur with the systems with valves and filters adopted up to now, where the very external structure of these elements constitutes a mechanical connection between the watermain and the plant which in some cases permits the passage of bacteria or pollutants.

BRIEF DESCRIPTION OF THE DRAWINGS

In the drawing is illustrated an exemplary embodiment of the invention in which FIG. 1 is a diagrammatic view of the back-flow prevention device forming the subject of the invention.

DESCRIPTION OF THE PREFERRED EMBODIMENTS

The air gap is created in a simple way, using a tank which is filled, generally by gravity, with water coming from an inlet in the watermain. The free surface of the water in the tank is constantly maintained below the inlet; floats or other systems already in common use would probably be employed for this purpose.

Water is taken from the tank for use in the dental clinic. This operation may be performed by means of a pump, or by gravity if the tank can be placed higher than the dental clinic. During normal functioning, water falls into the tank and is sent to the dental clinic. It has been evidenced that neither bacteria nor pollutants are able to find their way up the resulting jet and into the watermain.

In the case of an interuption in water flow, an air gap is created between the inlet and the tank; this gap prevents the passage of bacteria and pollutants from the water in the tank (which could contain such pollutants since it is connected to the dental clinic) into the watermain.

Also in the case of siphoning or flow inversion, eventual bacteria and pollutants coming from the dental clinic could reach only the tank; neither bacteria nor pollutants can, under any circumstances, penetrate into the watermain. Using the back flow prevention system in question it is also possible to take the water coming out of the dental clinic and reintroduce it, by means of a recycling conduit, into the tank, so that it can be used again. A disinfection device of a type in common use might be placed on the conduit which could therefore disinfect the recycled water if this should contain percentages of bacteria or pollutants above a predetermined limit. The disinfection operation, even if not strictly necessary since the recycled water never comes into contact with the watermain, is particularly useful in cases in which a closed-circuit recycling plant is envisaged, where the watermain, once the plant is filled with water, is used only for occasional small refills of the water in the tank.

The possibility of effecting the recycling of the water used by the dental clinic, or indeed of using a closed-circuit recycling plant, represents a remarkable advantage of the disconnector in question both as regards water-consumption and with respect to the quantity of water which is sent to the drains, thus reducing pollution there. Notwithstanding its apparent simplicity, the disconnector in question provides the solution to a great problem which up to now had never been completely solved using the devices available. Modifications of a practical-applicational nature can be made to the present invention without changing the fundamental inventive idea behind it, as described in the claims which follow.

What is claimed is:

1. A back-flow prevention device comprising:
   a water supply means for supplying water to a dental clinic, said supply having a water inlet and a water outlet, means for fluidly connecting said water outlet dental instruments within said dental clinic, said water inlet being positioned to receive water by gravity from a water source, there being no mechanical connection between said water inlet and said water source.

2. A back-flow prevention device as in claim 1, in which the water inlet comprises a tank, having an open end, which receives the water from the water source, wherein the surface level of water in said tank is constantly maintained below the level of said water source and also including means for supplying water from said tank to said water outlet.

3. A back-flow prevention device as in claim 2, further comprising a recycling conduit means for receiving water from the dental instruments and returning water to the tank.

* * * * *